United States Patent [19]
Poli et al.

[11] Patent Number: 5,654,000
[45] Date of Patent: Aug. 5, 1997

[54] PHARMACEUTICAL COMPOSITIONS FOR TRANSMUCOSAL DELIVERY OF PEPTIDES

[75] Inventors: Stefano Poli; Federico Mailland; Luigi Moro, all of Quinto De'Stampi, Italy

[73] Assignee: Poli Industria Chimica S.p.A., Milan, Italy

[21] Appl. No.: 693,620

[22] Filed: Jul. 17, 1996

Related U.S. Application Data

[63] Continuation of Ser. No. 374,702, Feb. 22, 1995, abandoned.

[30] Foreign Application Priority Data

Jul. 28, 1992 [IT] Italy ............................ MI92A1831

[51] Int. Cl.$^6$ .................................................. A61K 9/127
[52] U.S. Cl. .................................. 424/450; 436/829
[58] Field of Search .................... 424/450; 436/829, 436/70.11; 514/772, 772.3, 772.4

[56] References Cited

U.S. PATENT DOCUMENTS

| | | | |
|---|---|---|---|
| 4,944,948 | 7/1990 | Uster et al. | 424/450 |
| 5,342,625 | 8/1994 | Hauer et al. | 242/455 |
| 5,369,131 | 11/1994 | Poli | 514/772.4 |
| 5,401,511 | 3/1995 | Margolit | 424/450 |

FOREIGN PATENT DOCUMENTS

| | | |
|---|---|---|
| 0177223 | 4/1986 | European Pat. Off. |
| 0386960 | 9/1990 | European Pat. Off. |
| 26601992 | 10/1991 | France |
| 9000048 | 1/1990 | WIPO |

OTHER PUBLICATIONS

*Sustained-Release Drug Delivery Systems, Remington's Pharmaceutical Sciences*, 18th Ed. pp. 1691–1692, 1536, 271–272 (1990).

S.H. Chen et al.; *Micellar Solutions and Microemulsions: Structure, Dynamics, and Statistical Thermodynamics*, pp. 161–164 (1990).

G. Gregoriadis; *CRC Liposome Technolog vol. I, Preparation of Liposomes*, pp. 1–17 (1st ed. 1984, 2d ed. 1993).

*Liposomes; a practical approach*, eds. R.R.C. New, pp. 1–33 (1990).

G. V. Betegeri et al.; *Liposome Drug Delivery Systems*, pp. 1–25 (1993).

F. J. Martin; *Specialized Drug Delivery Systems, Drugs and the Pharmaceutical Sciences* 41:267–272 (1990).

*Pharmaceutical Dosage Forms: Disperse Systems*, vol. I, pp. 49–55, 263–277, 353–354 (1989).

*Pharmaceutical Dosage Forms: Disperse Systems*, vol. II, pp. 335–350, 567–594 (1989).

*Colloidal Drug Delivery Systems, Drugs and the Pharmaceutical Sciences*, ed H. Lieberman et al. 66:31–121 (1994).

*Microemulsions: Theory and Practice* ed J. Kreuter, pp. 1–19, 51–77 (1977).

Primary Examiner—Gollamudi S. Kishore
Attorney, Agent, or Firm—Bell, Seltzer, Park & Gibson

[57] ABSTRACT

Liquid bioadhesive microemulsions or liposomic dispersions containing proteinic substances, especially calcitonin, that allow the systemic, local or topical administration of drugs by transmucosal route are described. This type of administration shows some considerable advantages of activity, tolerability, dosage individualization and drug stability. The compositions contain proteinic substances, and a polyoxyethylene-polyoxypropylene thermosetting copolymer. At body temperature the viscosity of the compositions is increased and provides increase residence time at the administration site.

13 Claims, 2 Drawing Sheets

PHARMACEUTICAL COMPOSITIONS FOR TRANSMUCOSAL DELIVERY OF PEPTIDES

The instant application is a continuation of U.S. patent application Ser. No. 08/374,702, filed 22 Feb. 1995, now abandoned the disclosure of which is hereby incoporated herein by reference in its entirety.

The present invention relates to pharmaceutical compositions in the form of microemulsions or liposomic dispersions for the transmucousal administration of proteins or peptidic substances which are pharmacologically active; they differ from the known liposomic or microemulsified compositions in that they contain addition a thermosetting agent able to enhance the residence time on the administration site and, consequently, to promote the absorption of the delivered drug.

BACKGROUND OF THE INVENTION

The administration of proteinic substances has been, from a few years ago, limited to the parenteral route as it was the only one which provided a good absorption to molecules having a complex structure and not able to tolerate environments with a high acidity and rich in proteolytic enzymes such as that ones which can be found in the digestive apparatus. The need to apply the proteinic substances by an invasive parenteral administration, the difficulty in obtaining, on a large scale, many proteins from natural sources, and the very high activity of such substances, with the consequent risks of overdosage, have limited use of such substances in clinical practice.

Recent attempts to orally administer the peptide substances with drug delivery systems such as microparticles and liposomes, did not obtain satisfactory results in absorption or reproduciblity of the same: the transit time variability in the digestive apparatus, associated with, the large presence of proteolytic enzymes, has made the researcher to consider oral administration as a problem.

More recently, in an attempt to avoid the more invasive parenteral administration, formulations suitable for nasal administration of proteinic substances have been proposed.

The typical disadvantage of this way of administration consists in: the relatively reduced area available for the absorption, the high clearance (which reduces the time of contact ) and the particular characteristic of the muconasal epithelium which covers the upper respiratory organs, that is the presence of cilia in association with mucus producing glands.

In addition, the "absorption promoters" frequently used in formulations for nasal administration produce damage to the mucociliary clearance of the deposit zone of the formulation and give problems in regard to repeated or chronic treatment cycles.

With the same aims, rectal administration of protein substances has also been proposed: this administration is nevertheless confined to the mediterranean area and is considered unproposable to the nordamerican and nordeuropean populations. In addition to the ethnical problem, the rectal ampoul has a limited surface and a basic pH.

More recently it has been found that intravaginal administration, till now considered for local treatment only, can be used to allow the systemic absorption of protein substances. The vaginal mucous is in fact able to allow the diffusion of considerable quantities of pharmacologically active substances from the application surface to the dermic stratum which has a rich vascular area able to absorb and drain in the systemic circle, besides the deep dermic stratum.

An important characteristic which allow high absorption values in the vaginal area, as well as for nasal cavity and mucous in general, is the bioadhesion of the formulation.

The formulations commonly used in medical practice take advantage of the vehicle characteristics: its viscosity and composition play an important role on the time of persistence of the drug, and hence effective amount, in the absorption area, as well as the achievement of an opportune absorption area and the extension of the same.

Generally, the lower the mobility of the vehicle, and the higher its viscosity, the more the persistence permanence time increases, and, consequently, the higher the possibility that the active substance is quantitatively absorbed.

Nevertheless, we must not neglect the fact that, usually, a reduced viscosity helps to spread the dispersion of the dosage applied by means of suitable mechanical devices, such as the nasal minipump or foam generators, allowing a very fine distribution of the product. This is very important to increase the contact surface and promote drug absorption.

SUMMARY OF THE INVENTION

The objects of present invention are pharmaceutical compositions in the form of microemulsions or liposomic dispersions characterized by the fact that contain a thermosetting agent able to allow a product viscosity increase with temperature, thus allowing a longer mucousal residence time and enhanced drug absorption profile.

Due to the thermosetting properties of the vehicles it is possible to make pharmaceutical compositions which have a reduced viscosity at room temperature, helping the distribution of finely absorbed divided product on a larger surface. When the composition reach the mucous a structural change takes place as a function of the body temperature, i.e. the viscosity of the product increase, thus, providing a large persistence of the system on the absorption zone.

The use of formulations that are liquid at room temperature but which increase their viscosity with temperature giving semi-solid products when warmed to body temperature is already known.

There are, in fact, some patents that describe the use of a particular polymer (Pluronic) to reach that goal.

As an example, U.S. Pat. No. 4,478,822 describes a vehicle useful to deliver a medicament to a body orifice, with a drug delivery system consisting of a clear liquid which forms a semi-solid gel at human body temperature.

The desired sol-gel transition temperature of the solution can be modified by changes in polymer concentration or in chemical characteristics of the solution.

We have surprisingly found that the same goal can be obtained also in systems more and more complex, like liposomes of microemulsions.

Normally, in this type of formulation it is difficult to balance the composition. In fact, microemulsions are a very complex system with the coexistence of at least three different phases: a disperse phase, an interface layer of surfactants and/or cosurfactants surrounding the disperse phase, and a continuous phase that contains the previous ones. The addition of relevant amounts of copolymer in order to obtain the sol-gel system transition, normally change dramatically the precise ratio between the four main components of the microemulsion system, that are water, surfactants, cosurfactants and oil. Only a formulation with a new balance point allows thermosetting microemulsions. The same problem, with due proportions and limitations, is also true to liposomic dispersion.

In a typical embodiment, the invention uses as thermosetting vehicle, a polyoxyethylene-polyoxypropylene copolymer, preferably the one known with the trade name of Pluronic F 127™ or Lutrol F 127™. These characteristics, which are favourable even when present in conventional solutions, are particularly important and effective when used in complex and modern vehicles such as the liposomic or microemulsion systems.

The liposomic systems, well-known for their potential of vectorization, consist in spherules, with very small dimensions, composed of concentric layers of phospholipidic material which are alternated to discrete and isolated aqueous spaces.

The high affinity with mucouses, typical of liposomic systems, is dramatically increased by the introduction of termosetting polymers, generating a product with bioadhesive characteristics which, by increasing the potential of vectorisation, leads to an improved activity.

For the liposomic products, that contain the polyoxyethylene-polyoxypropylene copolymer, the viscosity change induced by the temperature is reversible (FIG. 1).

That previously stated can also be extended to the microemulsionated systems too: the well proportioned combination of its constituent, essential from a structural point of view, with a polyoxyethylene-polyoxypropylene copolymer produces an "apparent solution" able to increase the viscosity when in contact with mucouses. The human body application of this system, following the partial solvent evaporation, generates a barrier which, owing to the thermosetting gelation, promotes the bioadhesion of the system.

Even in this case the transition temperature from the sol condition to the gel is reversible (FIG. 2).

Thus, objects of the present invention are pharmaceutical compositions useful for transmucousal administration, in particular vaginal or nasal, of proteinic or peptidic substances, pharmacologically active. Examples of similar substances include calcitonin, insulin, desmopressine, interleukin, interferon, GMCSF (granulocite monocite colony stimulating factor), ciclosporin, posatirelin, protirelin, timopentin, pidotimod, mono or polyclonales antigenes, antigenic proteins of bacterial or viral origin, parathormon, gonadorelin, coagulation factors, epidermic growth factors, "insulin like" growth factor, endorphin and their derivatives or fragments, tioxoprolylcysteine, tioxoprolylthiazolidincarboxylic acid, irudine and their derivatives.

DESCRIPTION OF PREFERRED EMBODIMENTS

Figure 1:
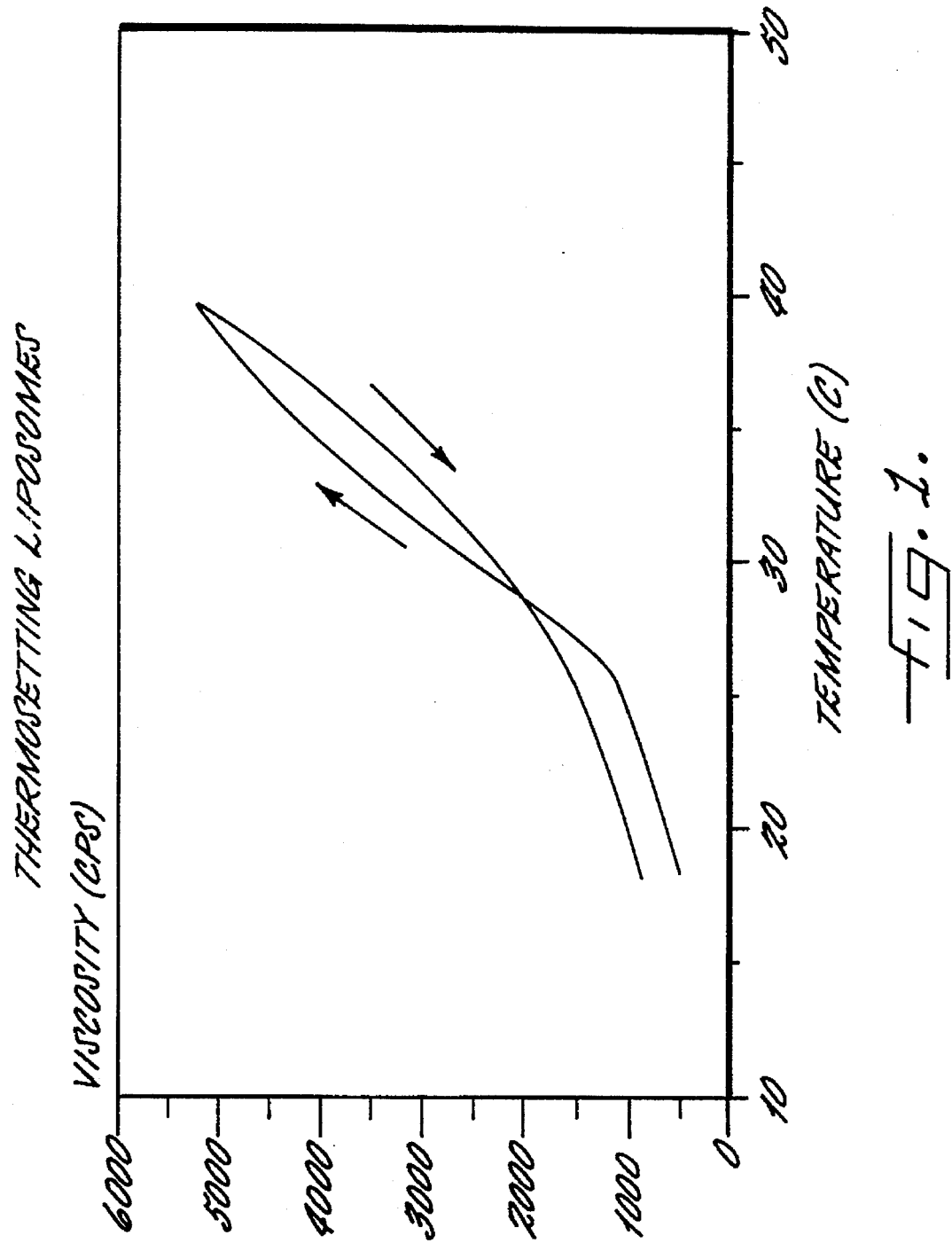
FIG. 1 is a graphical representation of changes in viscosity with temperature of the present liposomes.
Figure 2:
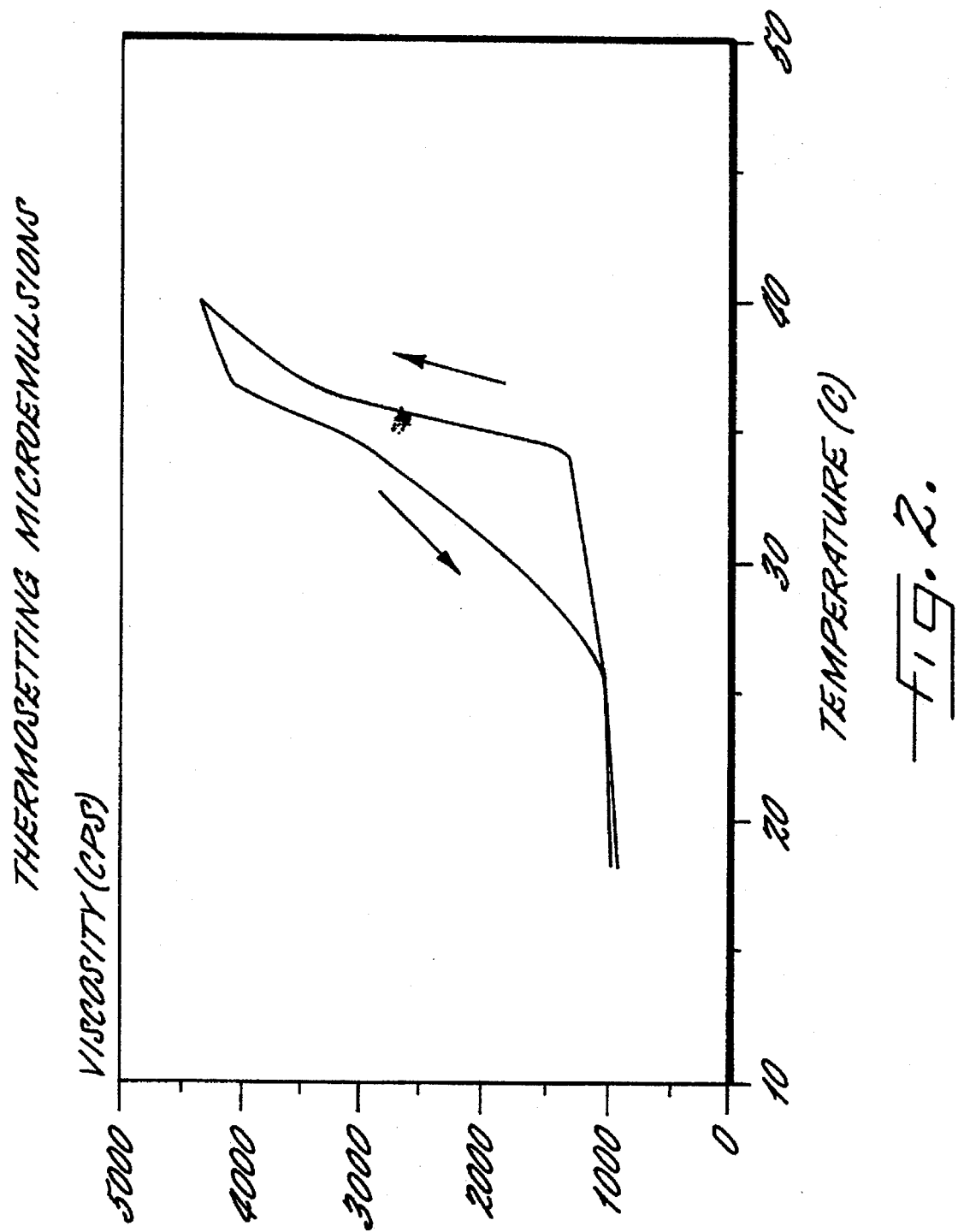
FIG. 2 is a graphical representation of changes in viscosity with temperature of the present microemulsion.

The pharmaceutical compositions, in accordance to the invention, can be in any form suitable for vaginal or nasal administration, such as soft gelatine vaginal capsules, vaginal suppository composed of natural or semi-synthetic glycerides, creams, gels, emulsions, suspensions, solutions, foams.

The liposomic systems can contain:
modulators of transition temperature of phospholipids, such as cholesterol and its derivatives;
antioxidant agents such as tochopherols, and their esters, BHA, BHT, carotenes;
stabilizer agents;
preservatives;
an alcoholic solvent phase;
eventual auxiliary substances, such as pH correctors, moisturizers, perfumes, essences.

The microemulsion systems, in addition to the components already mentioned and to the polyoxyethylene-polyoxypropylene copolymer, could contain excipients known by the experts with the names of antioxidant, stablizer, preservatives, buffers, and so on.

Obviously, the administration of liposomic and microemulsionated systems will be made easier by the use of suitable spray dispensers or applicators in the form of a cannula, syringe or similar devices.

According to a preferred embodiment of the invention, the compositions will contain stabilizer or absorption promoter, polygalacturonic acid, polyglucuronic acid, hyaluronic acid, hyaluronamine, hyaluronamide or their salts and pharmaceutical acceptable derivatives.

In vivo experimental studies employing products relevant to the invention, have shown that the intravaginal or nasal route allow a systemic bioavailability comparable with that achievable by a parenteral administration, without presenting the limits of this route. As a consequence the dosage potency of proteins or peptidic substances, pharmacologically active, by vaginal or nasal administration will be substantially similar to those already used for the well-known administration routes. By using pharmaceutical forms not exactly metered, such as solutions, creams or gel, according to the invention, it is possible to obtain a personalization of the dosage: considering the often high pharmacological activity of the protein substances, this gives important advantages related to the reduction of the risks of overdose.

According tea preferred embodiment, the invention gives pharmaceutical compositions suitable to the vaginal or nasal administration containing as an active ingredient a calcitonin of any source.

The high bioavailability level achievable by the vaginal administration of a calcitonin products relevant to the invention, with a proper bioadhesion, is shown by a pharmacological experiment. The decrease of calcemic level in rabbit serum after vaginal application of: a) a simple solution, b) a thermosetting gel and c) a thermosetting gel furtherly thickned with hyaluronic acid, has been measured. As a reference the decrease of calcemic serum level obtained by administration of an equal dose of the same drug by i.m. route (see tab. 1) was chosen.

TABLE 1

| ADMINISTRATION | | CALCEMIC LEVEL VS BASAL VALUE | |
| --- | --- | --- | --- |
| TYPE | ROUTE | AREA (cm$^2$) | % VS I.M. |
| Solution 100 I.U. | i.m. | 444 | 100 |
| Solution 100 I.U. | vaginal | 264 | 60 |
| Gel(Pluronic F127) 100 I.U. | vaginal | 439 | 99 |
| Gel(High m.w. Hyalur.Acid)100 I.U. | vaginal | 425 | 95 |

The demonstration of a systemic absorption of proteic substances, when administrated by vaginal or nasal route employing liposomic or microemulsions bioadhesive preparations, make possible a vaccine-therapy uninvasive or other forms of immunitary protection using antigen substances.

It is well-known that the oral administration of drugs meets the compliance of patients; but it is well-known too that a simple pharmaceutical oral dosage form cannot be employed with peptides or proteins. The object of the present invention is a pathway to bypass the limits of the oral route keeping a good compliance of the patients.

Neverthless the thermosetting liposomes or microemulsions not only are a drug delivery, system particularly usefull for peptides and proteins, but can be advantageously employed also for low molecular weight drug, like nicotine, FANS and so on.

The invention will have a more detailed description by the following examples.

EXAMPLE 1

Lecithin (4 g), and cholesterol (0.75 g) were dissolved in ethyl alcohol. Tocopherol acetate (0.02 g) was added to the solution. In an other container, sodium methylparaben (0.15 g), edetate disodium (0.1 g) and salmon calcitonin (7 mg) were dissolved in purified water (80 mL). The aqueous solution was added to the first one under stirring. The alcohol was evaporated by heating to form a liposomic dispersion. Thereto were added Lutrol F127 (13 g) and purified water (q.s. to reach 100 mL). The liposomic dispersion was subdivided in glass vials that following were closed with a minipump. A pre-arranged unit dose administration was so allowed.

EXAMPLE 2

Soybean lecithin (30 g), tocopherol acetate (500 mg) and cholesterol (2 g) were dissolved by heating in isopropyl alcohol. The solution was keeped at 50 ° C. until 50 mM citrate buffer (pH 4.5, 1000 mL) containing calcitonin (50 I.U./mL), beforehand heated at the same temperature, was added, to give a hydro-alcoholic phospholipid dispersion. The mixture was vigorously shaken under reduced pressure causing the evaporation of isopropyl alcohol and giving a liposomic dispersion of calcitonin. Hydroxyethylcellulose (10 g) was added and a gel, having a suitable viscosity for the vaginal application, was obtained.

EXAMPLE 3

Hyaluronic acid sodium salt (10 g) and Posatirelin (3.33 g) were dissolved in 50 mM citrate buffer (pH 4.5, 1000 mL). A suitable amount of Pluronic F127 was added, so to obtain an increased viscosity to body temperature. The gel formed shows a good clearless and can be applied into the vagina syringe dispenser.

EXAMPLE 4

Lecithin (6 g) was dissolved in a mixture of isopropyl myristate and ethyl alcohol (12.5 mL). After complete dissolution tocopherol acetate (0.02 g) was added. Thereto sodium cholate (4 g) was suspended. Into an other container sodium methylparaben (0.15 g) and calcitonin (7 mg) were dissolved in purified water (60 mL). Aqueous solution of calcitonin was added to lipophylic phase, maintained vigorously shaked. To the formed microemulsion, Pluronic F127 (15 g) was added and dissolved. A necessary amount of purified water to make the entire amount 100 mL was added. The microemulsion was optically clearless and shown a transition temperature sol-gel of about 30°–40° C.

EXAMPLE 5

Edetate disodium (0.15 g), sodium methylparaben (0.225 g) and salmon calcitonin (12 mg) were dissolved in purified water (100 mL). A solution, was obtained by dissolving lecithin (5.6 g), cholesterol (1.12 g) and tocopherol in slightest amount needed of ethyl alcohol, and added. Thereto polyoxyethylene-polyoxypropylene copolymer (Pluronic F127, 19.5 g) was dissolved, and a necessary amount of purified water to make the entire amount 150 mL was added. The liposomic dispersion was subdivided into aerosol pressurizated container giving a thermosetting liposomic foam.

EXAMPLE 6

Lecithin (30 g) and nicotine (3.8 g) were dissolved in a mixture of isopropylmiristate and ethyl alcohol, keeping at 50° C. until dissolution. After complete dissolution tocopherol acetate (0.6 g) was added and sodium cholate (15 g) was suspended. Into an other container sodium methylparaben (0.5 g) and sodium edetate (0.5 g) were dissolved in pre-heated (60° C.) purified water (300 mL). Aqueous solution was added to lipophilic phase, maintained vigorously shaked. The formed microemulsion was cooled to 5°–10° C. then Pluronic F127 (75 g) was added and dissolved. A necessary amount of purified water to make the entire amount 500 mL was added. The microemulsion, that shown a transition temperature sol-gel of about 30°–40° C., can be applied on the skin or on the nasal mucousal with a suitable device.

We claim:

1. A liquid pharmaceutical composition suitable for protein or peptide drug administration on a body surface comprising:

(a) a liposomic dispersion containing the drug; and (b) a thermosetting copolymer capable of enhancing viscosity of the composition from above about 500 cps to about 10,000,000 cps at body temperatures, said thermosetting copolymer consisting of a polyoxyethylene-polyoxypropylene copolymer.

2. A composition according to claim 1, wherein the drug is absorbable through skin or mucosal membranes.

3. A composition according to claim 2, wherein the drug is absorbable through vaginal mucosal tissue.

4. A composition according to claim 2, wherein the drug is absorbable through nasal mucosal tissue.

5. A composition according to claim 2, wherein the drug is absorbable through rectal mucosal tissue.

6. A composition according to claim 1, wherein the polyoxyethylene-polyoxypropylene copolymer is contained in the composition in a range between 10% and 30% w/w.

7. A composition according to claim 1, wherein the drug is selected from the group consisting of calcitonin, insulin, desmopressine, interleukin, interferon, granulocyte, monocyte colony stimulating factor, cyclosporin, posatirelin, protirelin, timopentin, antigens, parathormon, gonadorelin, coagulation factors, epidermic growth factors, insulin growth factor, endorphins, endorphin fragments, and thioxoprolylcysteine.

8. A composition according to claim 1, wherein the drug is a calcitonin.

9. A composition according to claim 1, wherein the drug is an antigen or antibody suitable for use in immunotherapy.

10. A composition according to claim 1 containing absorption enhancers or stabilizers selected from the group consisting of polygalacuronic acid, polyglycuronic acid hyaluronic acid, hyaluronamide, and pharmaceutically acceptable salts thereof.

11. A composition according to claim 1 in the form of a dermal or vaginal foam.

12. A composition according to claim 6, wherein the range is between 13% and 20% w/w.

13. A composition according to claim 1, wherein said thermosetting copolymer is capable of enhancing the viscosity of the composition from about 500 cps to about 1,000,000 cps.

* * * * *